United States Patent [19]

Schlein

[11] Patent Number: 4,516,322
[45] Date of Patent: May 14, 1985

[54] SHEARING APPARATUS

[76] Inventor: Allen P. Schlein, 107 Curtis Ter., Fairfield, Conn. 06430

[21] Appl. No.: 423,729

[22] Filed: Sep. 27, 1982

[51] Int. Cl.$^3$ .............................................. B23D 21/06
[52] U.S. Cl. ........................................ 30/92; 30/233; 30/228; 83/580; 128/92 R
[58] Field of Search .................. 30/92, 134, 203, 208, 30/210, 223, 228, 241–243; 83/198, 580; 128/92 R

[56] References Cited

U.S. PATENT DOCUMENTS

| | | | |
|---|---|---|---|
| 2,563,069 | 8/1951 | Roberts | 30/92 |
| 3,024,530 | 3/1962 | Haskell et al. | 30/228 X |
| 3,861,035 | 1/1975 | Ramey et al. | 30/92 |
| 3,972,116 | 8/1976 | Forsythe et al. | 30/228 |

Primary Examiner—Douglas D. Watts
Attorney, Agent, or Firm—Spencer E. Olson

[57] ABSTRACT

A mechanically operated cutter assembly adapted to shear bar or rod stock, such as bone pins, even though both ends of the rod are fixed, along a plane perpendicular to its axis, includes a body member having an elongated interior channel within which a rod carrier and cutting plug are slidably mounted, the body having a slot disposed transversely to the longitudinal axis of and intersecting the interior channel for permitting access of the rod to the cutting plug. The cutting plug has a transverse passageway contoured to fit a portion of the periphery of the rod to be sheared which, in a first longitudinal position is aligned with the rod-receiving slot. The cutting plug is adapted to be moved to a second longitudinal position at which the passageway is out of registry with the slot, whereby a rod carried in the passageway is severed. The tendency of the rod to bend during shearing is restricted interiorly of the body member by coaction of a transverse passageway in the rod carrier with the passageway in the cutting plug, and is restricted exteriorly of the body member by an arm secured to an external surface of the body member in a position to engage the rod near the point of shear.

11 Claims, 8 Drawing Figures

SHEARING APPARATUS

BACKGROUND OF THE INVENTION

This invention relates to shearing apparatus and, more particularly, to apparatus for severing bar or rod stock, such as bone pins or other elongate elements, along a plane transversely of the longitudinal axis without imposing twisting or other forces upon the element during severing.

Heretofore, devices for shearing rod stock such as bone pins and similar other cylindrical elements, which are often formed of stainless steel or titanim alloy having extreme hardness and thus difficult to cut, have included saws, abrasive cutters, manually operated shears and the like, which may be satisfactory for usage in some instances with rods of small diameter, but are difficult to use, and frequently unacceptable in other applications requiring the shearing of hard, larger diameter rods or pins. For example, in certain orthopedic applications, such as the fixation of fractures of large bones, in which the intramedullary bone pins typically have a diameter of one-fourth to three-eighths inch, manually operated shears are unsatisfactory because of the length of the handles required to develop the forces necessry to shear a rod of this diameter. Furthermore, an open cutting mechanism such as a shear tends to bend rather than cut the member, the bending not only increasing the area of the plane of shear and increasing the force required to sever the member but also resulting in dissipation of energy in effecting the bending which otherwise would contribute to the shearing force. Among the practical disadvantages of manually operated shears, even if the handles can be made sufficiently long to enable cutting of larger diameter rods, is that they frequently leave a jagged and distorted end after severing, an unacceptable result in orthopedic applications. Known rotatable pin cutters, although causing less bending than open shears during the severing operation, also frequently leave a jagged end after severing and are otherwise unsatisfactory for many cutting operations. Devices of this type comprise a rotatable pin cutter plug positioned within a cutter body, the body and cutter plug being relatively rotated by movement of handles attached to each of the elements. The rod or pin to be sheared is placed into a passageway in the cutter plug, which is initially aligned with an aperture in the cutter body, and shearing is accomplished by manually rotating the elements with respect to each other. When rods of relatively large diameter are involved, long handles are required to develop sufficient force to shear the rod, making the device cumbersome and under some circumstances unusable, as for severing a pin already implanted in the bone of a patient.

Among the applications in which abrasive cutters are used to sever rod or bar stock is the cutting of test pieces for tensile strength and/or other analysis of the bar material. However, the heat generated by this cutting method may sufficiently alter the surface characteristics of the material being severed as to preclude an accurate analysis of the material in an uncut rod. An efficient shearing device dissipates much less heat than does an abrasive cutter, sufficiently less that the surface characteristics are not appreciably affected, making shearing an acceptable technique for the cutting of test specimens and creating the need for efficient and conveniently usable shearing apparatus.

A shearing device described in U.S. Pat. No. 3,972,116, designed primarily for the shearing of bone pins and which overcomes the described disadvantages of manually operated shears and rotatable pin cutters, employs relative translational movement between a cutter and a cutter body. The described shear comprises an interfitting assembly of an elongated cutter body having an interior channel in which a cutter plug is slidably mounted. The body member has apertures intersecting the internal channel for receiving a pin and the cutter plug has a pin passageway therethrough. In a first longitudinal position of the cutter plug, perparatory to receiving the pin, the aperture and passageway are aligned and in a second position they are out of registry. The body member encloses the cutter plug to provide a close interfit between them whereby a cylindrical element, such as a bone pin, placed in the apertures and passageway in the first longitudinal position of the plug is severed by movement of the cutter plug to the second position; the apertures and passageway are sized to closely interface with the peripheral surface of the pin so as to substantially eliminate the tendency of the pin to bend at the point of shear. Relative movement of the cutter plug and cutter body is produced by a pneumatically operated mechanism which may include means for force multiplication.

Although the apparatus disclosed in U.S. Pat. No. 3,972,116 is effective in minimizing bending at the point of shear, its use is limited to those applications in which the pin to be sheared has a free end for insertion into the aligned aperture and passageway; thus, the device is unusable in situations where the rod or other elongated element, such as spinal rods which are implanted or fixed at both ends and which sometimes have to be cut to effect an adjustment. The problem of severing an elongated element having both ends fixed is also found in industrial applications, such as interlocked netting of the kind used for the reinforcement of concrete formed of relatively large diameter rods, or the standing rigging of sailboats, or steel cable. Thus, there is a need for shearing apparatus capable of severing or cutting rigid metal rods or pins the ends of which are fixed or otherwise inaccessible which, at the same time, does not have a tendency to bend the rod at the point of shear. Moreover, such shearing apparatus should be relatively small and compact, yet rugged, so as to be capable of severing bone pins, or other rod elements, in locations where working space is limited.

The shearing apparatus of the present invention utilizes the effective shearing properties of the shear described in U.S. Pat. No. 3,972,116 by, in effect, replacing the apertures in the body member with an open slot formed in the wall of the body member for receiving the rod to be severed, and replacing the passageway in the cutter plug with an open-sided rod-receiving slot. However, these changes, without more, would result in the rod not being sufficiently enclosed to prevent the tendency of the rod to bend at the point of shear as the cutter plug is moved relative to the cutter body. In other words, if the position of the apertures and cutter plug passageway were displaced sufficiently to form an open slot in a wall of the patented cutter (a modification not suggested in the patent), approximately half of the periphery of the rod received in the slot would be unenclosed, thus allowing it to bend under the extreme forces present during the shearing action.

It is an object of the present invention to provide shearing apparatus essentially having the shearing properties of the described prior art shear, yet capable of severing a rod or other elongate element whose ends are inaccessible for insertion in the shear, without racking or twisting the element. Another object of the invention is to provide a shear that is relatively small and compact yet rugged, and capable of severing rods or pins in locations where working space is limited.

SUMMARY OF THE INVENTION

Briefly, the improved shear according to the invention comprises an assembly of a body member having an internal longitudinal channel within which a pin carrier and a cutting plug are slideably mounted for movement along the longitudinal axis, the body having an open slot in one wall disposed transversely of the channel axis, and communicating with the channel, for receiving the pin to be severed. The pin carrier has a transverse passageway contoured to closely interfit with a portion of the circumference of the pin to be severed, which, in a first longitudinal position of the pin carrier is aligned with the slot so as to receive the inserted bone pin or other element. The cutting plug also has a transverse passageway contoured to closely interfit with a portion of the circumference of the pin, and during the shearing operation cooperates with the pin carrier passageway to encircle and firmly engage the pin. The movement of the cutter plug and pin carrier relative to the body is induced by a mechanical force multiplication device, such as a screw threadably engaging the body and projecting into one end of the channel.

In operation, with the pin initially engaged by the pin carrier passageway, the cutting plug is moved along the channel toward and into engagement with the pin carrier to establish the cooperating relationship between the pin carrier and cutter plug passageways, and upon further movement of the cutting plug and pin carrier and the pin engaged thereby to a second position at which the passageways are out of registry with the slot, the pin is severed by shearing action of the mating surfaces of the cutter plug and the internal channel. The pin carrier, closely interfitting and moving with the cutter plug, and both closely interfitting with the channel, constitutes internal means for restricting bending moment in the pin inherent in the shearing action. External bending moment restriction is provided by an arm pivotally joined to the outer wall of the cutter body and having a passageway for engaging the pin near the point of shear.

Other objects, features and advantages of the invention will become apparent, and its construction and operation better understood, from the following description of the preferred embodiment in conjunction with the accompanying drawings.

DESCRIPTION OF THE PREFERRED EMBODIMENT

Figure 8:
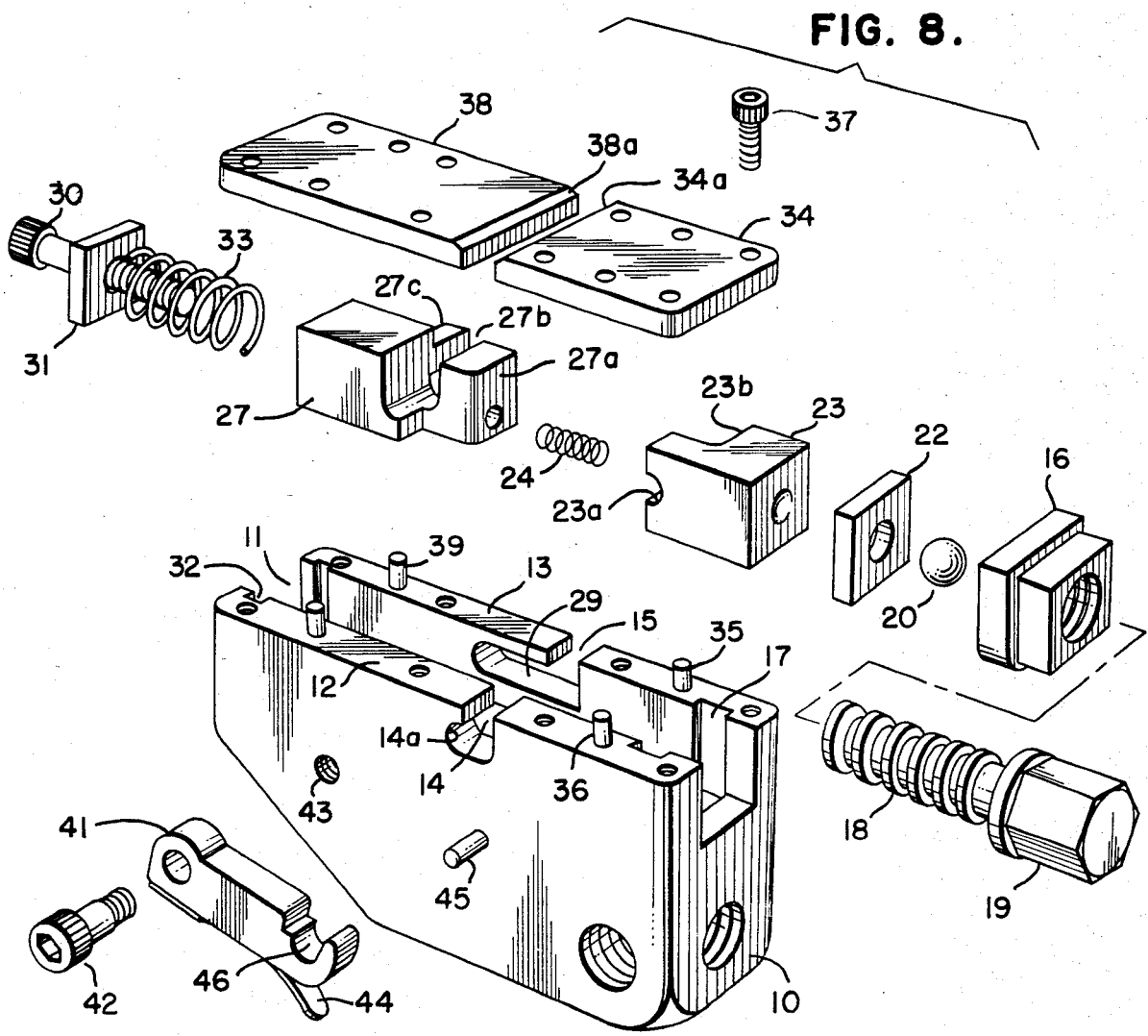
FIG. 8 is an exploded perspective view of the apparatus of this invention.

Referring to the drawings, wherein like numerals indicate like parts, and particularly FIG. 8 thereof, the pin shear includes a cutter body 10 formed of heat tempered steel, for example, to withstand the forces to which it is subjected when cutting a bone pin or the like. Body 10 has a longitudinal channel 11 therein extending the full length of the body, the channel having sidewalls 12 and 13 which respectively have aligned slots 14 and 15 formed therein which extend transversely of the long axis of body 10. The generally rectangular flange 16 of a threaded nut is received in a transverse slot 17 formed in walls 12 and 13 and in the bottom of channel 11, and a screw 18, preferably having an Acme thread, is threaded into the nut 16 and adapted to be turned by a suitable wrench (not shown) engaging the screw head 19. The inner end of screw 18 engages a thrust bearing, such as a ball-bearing 20, centered in a plastic centering plate 22 dimensioned to engage the inner walls of channel 11, for transferring the force induced by the screw to a vertically oriented surface 23a of a cutting plug 23 dimensioned to engage the surfaces of channel 11 with a sliding fit.

The vertically oriented surface of cutting plug 23 at the end opposite from surface 23a has a transverse passageway 23b formed therein, the passageway being semi-circular and having a radius substantially equal to the radius of the pin to be severed. The starting position of the cutting plug is determined by the length of a compression spring 24, one end of which is received in a recess formed in a vertically oriented surface 23b set back from the surface containing passageway 23a and the other end of which is constrained in a cylindrical recess 25 formed in a vertically oriented surface 27a of a pin carrier 27. The pin carrier 27 and cutting plug 23 are of the same nominal width, both being received in channel 11 with a sliding fit, and the width of pin carrier surface 27a is substantially equal to the width of surface 23b of the cutting plug. The pin carrier has a transverse pin-receiving passageway 27b formed therein, the passageway from the open end down having parallel planar side walls and the bottom being semicircular with a radius substantially equal to the radius of the pin to be severed.

The pin carrier 27 is adjustably positioned along the length of channel 11 by a screw 30 extending through a plate 31 secured in a transverse slot 32 formed in the walls of channel 11 and threadably engaging the pin carrier, and a compression spring 33 surrounding screw 30 and compressed between plate 31 and the pin carrier. The pin carrier is initially positioned with the side walls of passageway 27b aligned with the edges of slots 14 and 15 in the body 10; in this position, an integral protrusion 27c, one wall of which is an extension of one side wall of passageway 27b, is received with a sliding fit in a slot 29 formed in wall 13 and extending away from the cutting plug 23. The wall of slot 14 nearest the screw 18 is substantially perpendicular to the top surface of wall 12, the bottom is curved, and the opposite wall is undercut to form a semicircular recess 14a having a radius substantially equal to the radius of the pin to be severed.

The cutting plug 23 and pin carrier 27 are maintained in closely interfitting relationship within channel 11 by a pair of covers 34 and 38, dimensioned to close the channel on either side of slots 14 and 15. That is, the gap between the cover plates defines the open end of a transverse slot which extends into and intersects the channel to permit a bone pin 8 (FIG. 1) or other elongate element to be inserted into the passageway of pin carrier 27, even though it be anchored at both ends. In the illustrated embodiment, shown essentially full size, the slot depth is approximately one-half inch, making it possible to gain access to and sever a pin lying close to a patient's body. Plate 34, which is chamfered at 34a to facilitate insertion of the pin, covers the right end of the channel and is precisely located on the body by locating pins 35 and 36 and secured thereto by a plurality of screws, one of which is shown at 37. Plate 38 is positioned on locating pins 39 and 40 and when secured to the body with a suitable number of screws closes the channel to the left of the transverse slot; it is chamfered at 38a to facilitate pin insertion.

Exterior restriction of bending moment in the pin during shearing is provided by an arm 41 pivotally mounted on a screw 42 extending through the arm and threadably engaging an opening 43 in the wall of the body, the free end of which is normally urged into the vicinity of slot 14 by a leaf spring 44 secured to the underside of arm 41 and engaging the upper surface of a pin 45 projecting outwardly from the sidewall of body 10. A transverse passage 46 of semicircular shape having a radius substantially equal to that of the pin to be severed is provided near the free end of arm 41, and when the arm is in its "free" position, as shown in FIG. 1, the extremity of the arm partially covers the end of slot 14.

Figure 1:
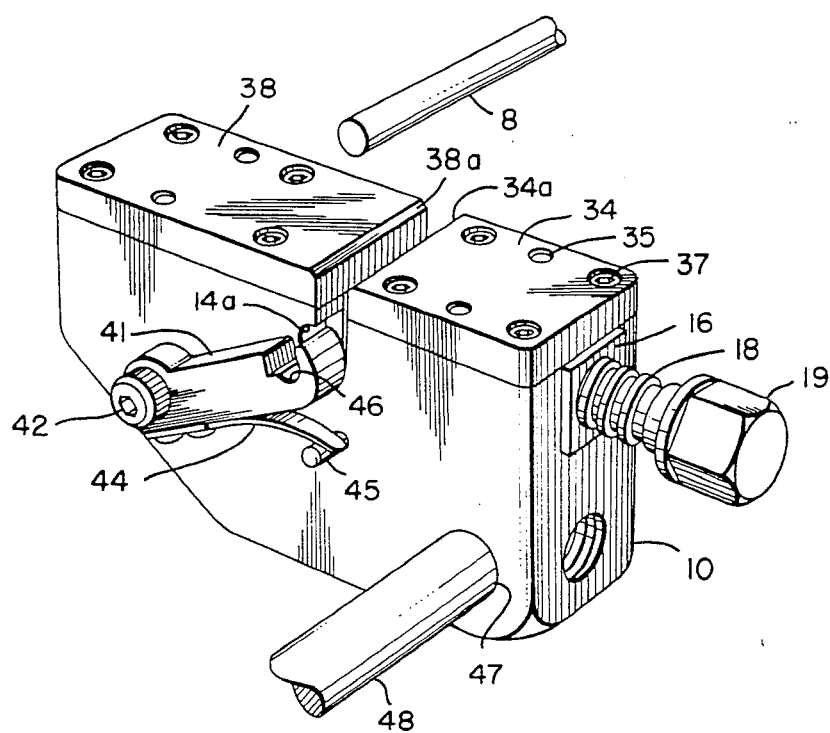
FIG. 1 is a perspective view of the pin shearing apparatus of this invention.
Figure 2:
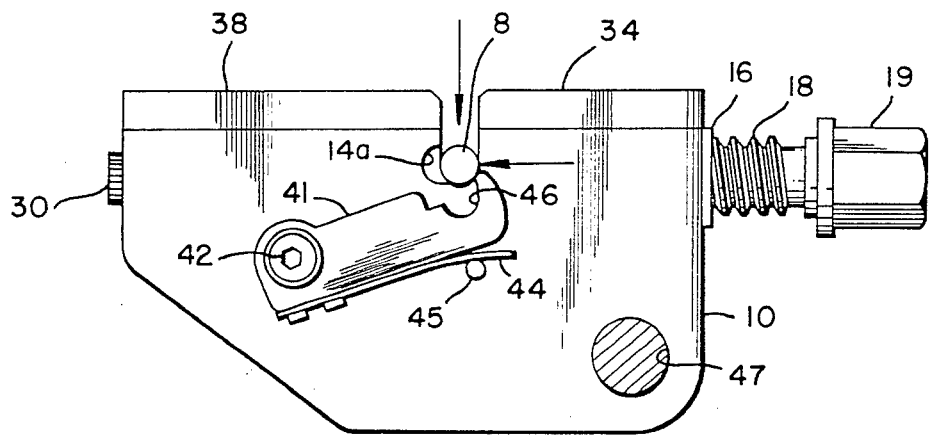
FIG. 2 is a side elevation view of the pin shear showing the initial position of the pin in the apparatus.
Figure 3:
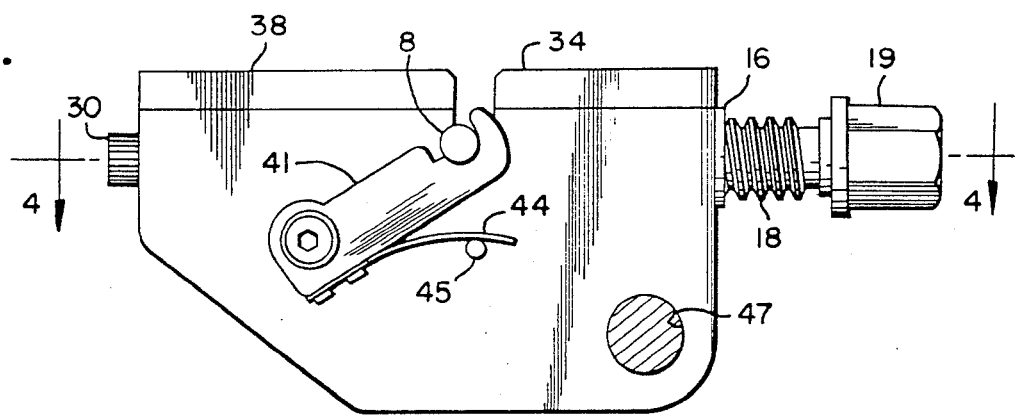
FIG. 3 is a side elevation view showing the pin in seated position in the apparatus.
Figure 4:
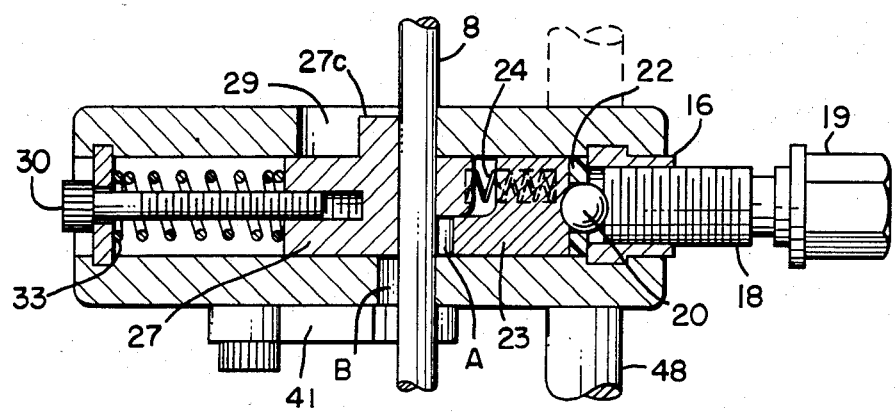
FIG. 4 is a cross-sectional view taken along line 4—4 of FIG. 3 showing the pin position illustrated in FIG. 2.

The operation of the shear will be evident from FIGS. 1–7 which show the positions of the pin carrier 27 and cutting plug 23 relative to the body 10 at four different stages of the severing action. Referring first to FIG. 1, the shear is maneuvered into engagement with the pin to be severed with the aid of a handle 48 threadably engaging an opening 47 in body 10, the handle also being used to counteract the tendency of the body to rotate in the direction of rotation of the screw 18 as it is turned clockwise to force the cutter plug 23 towards the pin. Two additional threaded openings for alternatively receiving the handle 48 are formed in the body, one directly opposite opening 47 and the other in the undersurface of body 10. FIGS. 2 and 4 show the relative positions of the elements of the shear immediately following insertion of pin 8 through the open slot and into the pin carrier passageway 27b. Pin carrier 27 is initially positioned by screw 30 and spring 33 so that the sidewalls of the pin passageway 27b are aligned with the corresponding sidewalls of the gap defined by the covers so as to allow the pin to be initially bottomed in the semicircular passageway. In this initial position, screw 18 is backed off to a point where compression spring 24 urges cutting plug 23 slightly away from pin 8, as is shown by the space labelled A, and by virtue of the offset of the semicircular portion 14a of slot 14, in this initial position the pin is not received in passageway 14a; this is best seen in FIG. 2, and is also evident from the space labelled B in FIG. 4.

Figure 5:
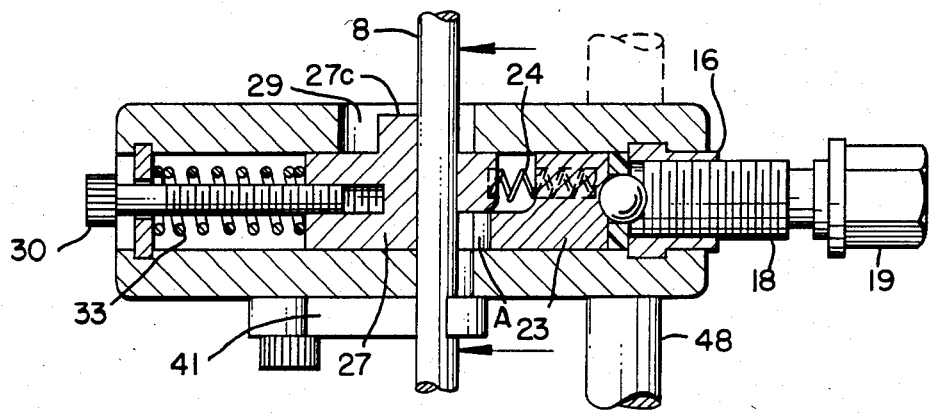
FIG. 5 is a cross-sectional view similar to FIG. 4 showing the pin position illustrated in FIG. 3.

The seating of the pin preparatory to shearing is illustrated in FIGS. 3 and 5 and is accomplished by urging the pin carrier and the pin 8 against the action of spring 33 in the direction of the arrows sufficiently to carry the pin into the semicircular portion 14a of slot 14; with the pin in this position the arm 41 is urged upwardly by its associated spring 44 and engages the pin in its passageway 46. The position of the screw 18 not having yet been altered, this slight movement of pin carrier 27 toward the left relieves some of the compression of spring 24, resulting in an enlargement of the space A between pin 8 and the forward edge of cutter plug 23.

Figure 6:
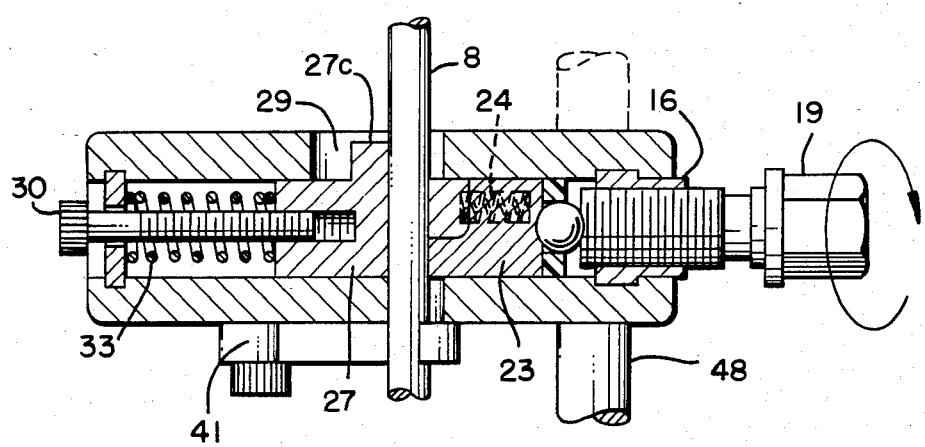
FIG. 6 is a cross-sectional view similar to FIG. 4 showing the pin in position for shearing.

Referring now to FIG. 6, upon rotation of screw 18 in the clockwise direction indicated by the arrow, a force is transmitted by ball-bearing 20 to the surface 23a of cutting plug 23 to move it to the left, and in so doing, compressing spring 24 so as to be completely contained in the recesses in the cutting plug and pin carrier, and forcing the surface 23b of the cutting plug into engagement with the vertical surface 27a of pin carrier 27. In this position, the semicircular cutting plug passageway 23a cooperates with the semicircular bottom of the pin carrier passageway 27b to substantially encircle that portion of pin 8 lying adjacent the inner surface of channel wall 12, the reminder of the interiorly contained pin being firmly engaged by the closely interfitting parallel side walls of pin carrier passageway 27b. Additionally, that exterior portion of the pin near the point of shear is maintained in firm contact with the semicircular passageway 14a in sidewall 12 by the passageway 46 in arm 41.

Figure 7:
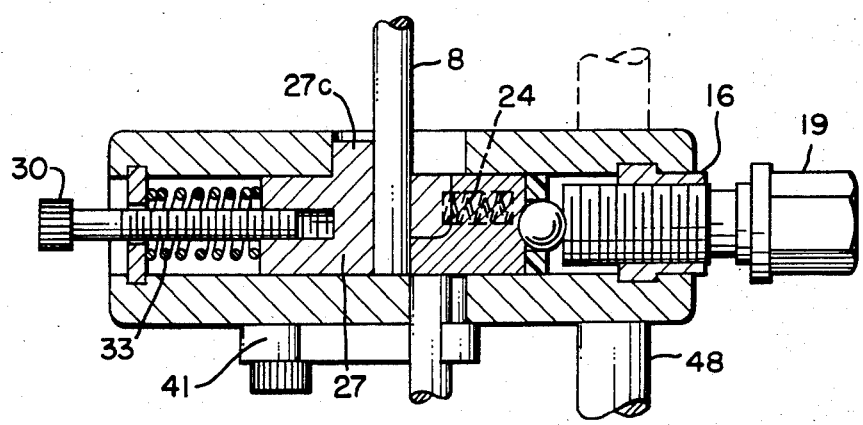
FIG. 7 is a cross-sectional view similar to FIG. 4 after activation of the force multiplication device and consequent shearing of the pin.

Thus, the pin is continuously and firmly engaged at either side of the point of shear, that is, both interiorly and exteriorly from the mating surfaces of the cutting plug and the inner surface of side wall 12 at passageway 14a, as the cutting plug is moved by continued screw rotation to the position shown in FIG. 7 to sever the pin. The pin carrier restricts interior bending of the pin, and arm 41 likewise continuously restricts the tendency of that exterior portion of the pin near the point of shear from bending in the direction opposite to that of the moving cutting plug. After the pin is severed, screw 18 is turned counterclockwise sufficiently to release its engagement with the pin and the device is removed from the pin, and upon further counterclockwise rotation of the screw, springs 24 and 33 return the cutter plug and pin carrier to the positions shown in FIG. 4.

While applicant has shown and described the present best embodiment of this invention, it will be apparent to one skilled in the art that the invention may take variant forms without departing from the scope and spirit of the appended claims. For example, although the described embodiment is designed to shear pins of circular cross section of fixed diameter, the passageways obviously can be dimensioned to accommodate circular cylindrical elements of other diameters, or elongate elements having other than a circular cross-section; that is, the passageways discussed above may be contoured to fit the specific cross-section of the element being severed. For example, in the well-known "Kirschner"-type bone pin, which has a fluted exterior surface, the passageways may be modified to substantially interface with the exterior flutes of the pin. Also, the shape and size of body 10 is subject to variation, subject, however, to the precaution that it have adequate mass for the material of which it is formed to withstand the extreme forces encountered during shearing action.

I claim:

1. A shear for cutting elongated elements such as bone pins and the like, said shear comprising:

an elongated rigid body member having an elongated interior cutting plug channel having first and second ends, sidewalls and a central longitudinal axis, said body member being closed except for an open slot disposed transverse to said longitudinal axis which extends from the exterior of said body member into said cutting plug channel for allowing access to said channel of an element to be sheared and except for a longitudinal slot in a first sidewall which intersects said transverse slot and which extends therefrom toward a first end of said channel in a direction parallel to said longitudinal axis;

pin carrier means slideably mounted in said cutting plug channel for longitudinal movement therealong between first and second positions, said pin carrier means having an open passageway therein which extends thereacross transverse to said longitudinal axis and is aligned with said open slot so as to be adapted to receive therein an element to be sheared when said pin carrier means is in said first position and to carry an element received therein along when said pin carrier means is moved from said first position to said second position;

cutter plug means slideably mounted in said cutting plug channel between its second end and said pin carrier means constructed and arranged to be moved into contact with with said pin carrier means and to coact with the pin carrier passageway so as to substantially encircle that portion of the length of an element supported in said pin carrier passageway which is nearest the sidewall of said cutting plug channel opposite that having said longitudinal slot and to be moved with said pin carrier means along said channel; and means supported on said body member at the second end of said channel for applying force to said cutter plug means for moving the cutter plug means, the pin carrier means and an element carried thereby toward said first end of said channel from said first position to said second position thereby to shear the element along a shear plane defined by the mating surfaces of said cutter plug means and the sidewall of said cutting channel opposite the sidewall having said longitudinal slot, said cutter plug means and said pin carrier means coacting to restrict bending in said element as it is sheared by movement of said cutter plug means from said first position to said second position.

2. A shear according to claim 1, further comprising means supported on the exterior surface of said body member opposite the surface having said longitudinal slot including means for engaging an exteriorly projecting portion of an element supported by the passageway of said pin carrier means for further restricting bending in the element as it is being sheared.

3. A shear according to claim 1, further comprising:
an arm supported on said body member arranged for applying force to a portion of an element supported in the pin carrier passageway and projecting from the exterior surface of said body member opposite the surface having said longitudinal slot in a direction to counteract the tendency of the element to bend as it is being sheared.

4. A shear according to claims 1 or 3, wherein said cutter plug means comprises a block having a passageway therein extending transverse to said longitudinal axis constructed and arranged to cooperate with the passageway of said pin carrier means to substantially encircle the element.

5. A shear according to claim 1, wherein said cutting plug channel has a given cross-section,
wherein at least a portion of the length of said pin carrier means has a cross-section corresponding to the cross-section of said channel, and
wherein said cutter plug means is an elongated member at least a portion of the length of which has a cross-section corresponding to the cross-section of said channel and has an open passageway extending transverse to said longitudinal axis for engaging an element supported in the pin carrier passageway.

6. A shear according to claim 5, wherein the confronting ends of said cutter plug and said pin carrier are shaped to mate together as the cutter plug means is moved along said channel into contact with said pin carrier means so as to position the transverse passageway in said pin carrier means relative to the open passageway in said cutter plug means so as to substantially encircle the element.

7. A shear according to claim 1 or 6, wherein said force applying means is a screw threadably engaging said body member and extending into said second end of said channel and engaging said cutter plug means.

8. A shear according to claim 1, further comprising:
an arm pivotally connected at one end to the exterior surface of said body member opposite the surface having said longitudinal slot for movement parallel to said surface and having a passageway therein near its other end shaped and arranged to apply force to an outwardly extending portion of an element supported in the pin carrier passageway in a direction to counteract the tendency of the element to bend as it is sheared by movement of said cutter plug means from said first position to said second position.

9. Apparatus for shearing elongated elements such as bone pins and the like, said apparatus comprising:
a rigid body member having an elongated interior cutting plug channel, said channel having first and second parallel sidewalls and parallel top and bottom walls joining said sidewalls, said body member being closed except for an open slot disposed transverse to the longitudinal axis of said channel and extending inwardly through the top wall of said channel and intersecting said channel for allowing access to said channel of an element to be sheared and except for an elongated longitudinal slot in said first sidewall which intersects and extends from said transverse slot toward a first end of said channel;
a pin carrier slideably mounted in said channel for longitudinal movement therealong between first and second positions, said pin carrier comprising a block-shaped member having an open passageway therein which extends transversely thereacross and is aligned with said open slot when said pin carrier is in said first position for receiving therein and supporting an elongated element inserted through said slot and for carrying the element along when said pin carrier is moved from said first position to said second position;
a cutter plug slideably mounted in said cutting plug channel between its second end and said pin carrier and adapted to be moved into contact with said pin carrier, said cutter plug comprising a block-shaped member constructed and arranged to coact with the walls of said channel and with the transverse passageway of said pin carrier so as to substantially encircle that portion of the length of an element supported in said transverse passageway which is nearest said second sidewall and to be moved along said channel with said pin carrier; and means supported on said body member at the second end of said channel for applying force to said cutter plug for moving said cutter plug into contact with said pin carrier and for moving said cutter plug, said pin carrier and the element carried thereby longitudinally along said channel toward said first end of said channel from said first position to said second position thereby to shear the element along a shear plane defined by the mating surfaces of said cutter plug and said second sidewall of said cutting plug channel, said pin carrier and said cutter plug coacting to firmly engage the element to thereby restrict the tendency of the element to bend as it is being sheared.

10. A shear according to claim 9, further comprising an arm pivotally connected at one to the exterior surface of said second sidewall for movement parallel to said surface from a rest position to an operating position, said arm having a passageway therein near its other end shaped and arranged to engage, when the arm is in the operating position, an outwardly extending portion of an element supported in the pin carrier passageway and to apply force thereto in a direction to counteract the tendency of the element to bend as it is being sheared.

11. A shear according to claim 9, wherein said shear further comprises:

an arm supported on said body member for movement from a rest position to an operating position for engaging, when the arm is in the operating position, a portion of an element supported in the pin carrier passageway and projecting from the exterior surface of said second sidewall and applying force thereto in a direction to counteract the tendency of the element to bend as it is being sheared.

* * * * *